United States Patent [19]

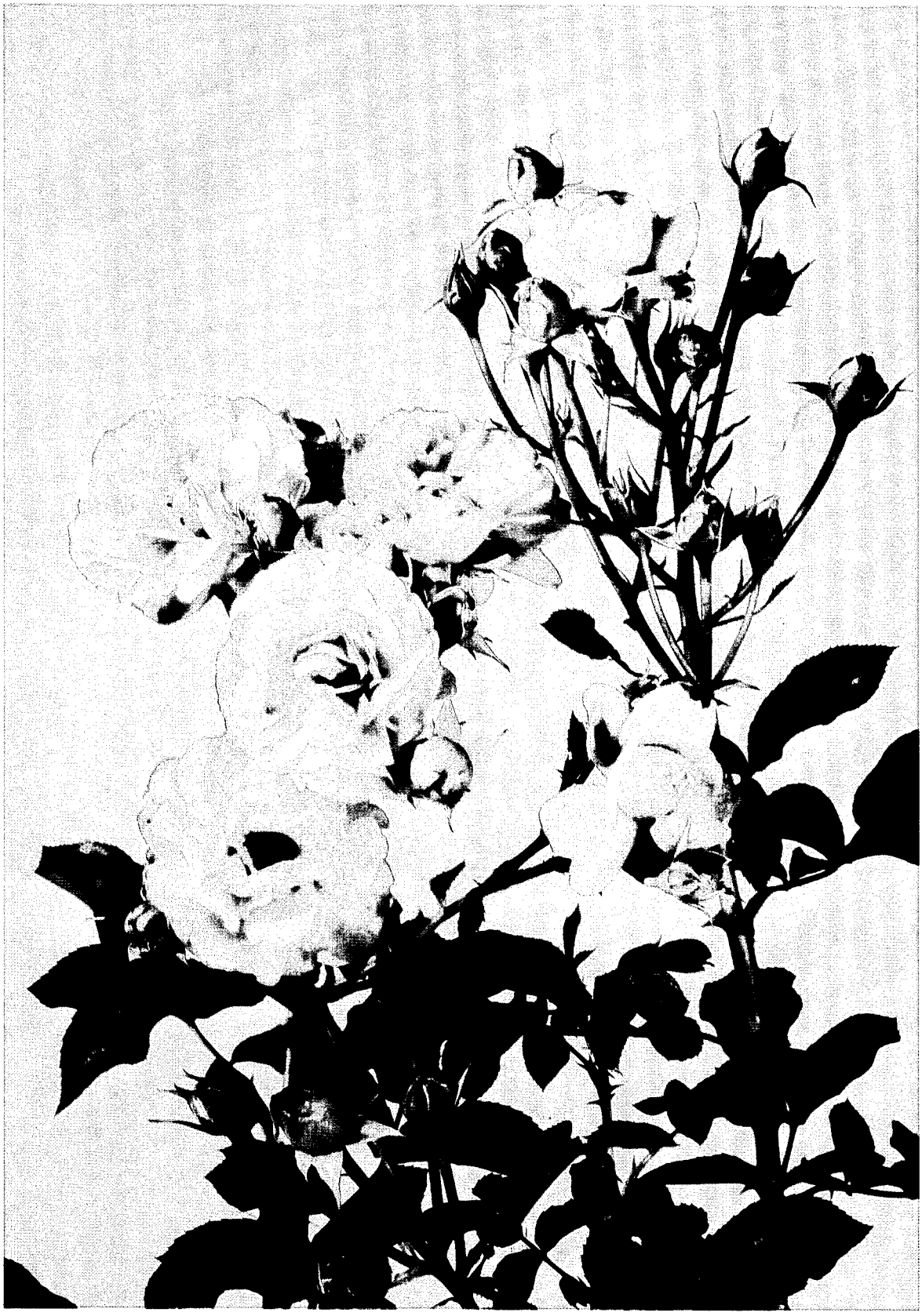

McGredy, IV

[11] Plant 4,297

[45] Sep. 5, 1978

[54] ROSE PLANT

[75] Inventor: Samuel McGredy, IV, Auckland, New Zealand

[73] Assignee: Armstrong Nurseries, Inc., Ontario, Calif.

[21] Appl. No.: 830,478

[22] Filed: Sep. 6, 1977

[51] Int. Cl.[2] ..... A01H 5/00

[52] U.S. Cl. ..... Plt./28

[58] Field of Search ..... Plt./28

*Primary Examiner*—Robert E. Bagwill
*Assistant Examiner*—James R. Feyrer
*Attorney, Agent, or Firm*—Andrew R. Klein

EXEMPLARY CLAIM

A low-growing hardy bush rose of the Floribunda type, raised as an outdoor seedling for garden decoration. The plant is bushy and vigorous, blooming almost continuously during the growing season. No evidence of susceptability to mildew has been observed, with respect to plants grown in Southern California. The peduncles have numerous stipitate glands and numerous fine hairs. The blooms are produced freely to abundantly and are double in character, numbering from 35–45 petals plus 3–8 petaloids. The bloom is a rich orange scarlet and it manifests an unusual degree of color stability, showing very little change or fading from the opening of the bud until the petals fall. It has a slight fruity fragrance.

1 Drawing Figure

1

This invention relates to a new variety of Floribunda rose. The plant is a hardy low-growing bush seedling raised outdoors for garden decoration. It was first propagated by Samuel McGredy, IV, in Portadown, Northern Ireland. The plant herein described was propagated in Ontario, Calif., from budwood derived from that first propagation. The description is based upon plants grown in Ontario, Calif.

The plant blooms freely to abundantly outdoors, and almost continuously during the growing season. It holds its distinguishing characteristics through succeeding propagations by budding, and bears its flowers sometimes singly, but usually from two to five or more on a stem, in irregular clusters on normal to strong, short to long, stems. The blooms have a slight fragrance, fruity in character. The plant is believed to be substantially resistant to mildew. No evidence of susceptability to this disease has been observed with plants grown in Southern California.

The seed parent of the new variety was Satchmo. Its pollen parent was an unnamed, undisseminated seedling derived from the following series of crosses:

((Hamburger Phoenix × Danse de Feu) × [Evelyn Fison × (*R. macrophylla coryana* × Tantau's Triumph)]).

The new rose variety differs from its seed parent, Satchmo, most outstandingly in petal count: the new rose is significantly fuller, with from 35 to 45 petals plus 3 to 8 petaloids, whereas Satchmo has only 23 petals on the average.

The new seedling rose differs in certain distinct ways from the following varieties which comprise the recent ancestry of its pollen parent. The pollen parent itself is no longer available for comparison:

Hamburger Phoenix is a climbing rose with long pointed buds, whereas the new rose is a Floribunda with ovoid buds.

Danse de Feu, also known as Spectacular, is a large-flowered climbing rose with 30 to 35 petals, whereas the new rose is a Floribunda with 35 to 45 petals plus 3 to 8 petaloids.

2

Evelyn Fison has only 10 to 12 petals, whereas the new seedling has significantly more petals, as described before.

*Rosa macrophylla coryana* is a climbing rose, a selected species; the new one, a Floribunda bush rose.

Tantau's Triumph, also known as Cinnabar, is an upright fairly tall-Floribunda with semi-double flowers, whereas the new rose is a low-growing Floribunda with double blooms.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is from short to average length, and average caliper, being erect and stiff with numerous stipitate glands and numerous fine hairs. The color is between Moderate Yellow Green, 2.5GY5/5, and Moderate Olive Green, 2.5GY4/3.

Before the calyx breaks, the bud is small to medium in size, short to medium in length, and ovoid in shape. The bud has small foliaceous appendages and its surface is covered with very fine hairs. Usually the slender foliaceous parts extend beyond the tip of the bud for a distance equal to one-quarter or more of its length.

As the calyx breaks, the color is near Dark Red, 5R3/7.

The inner surface of the sepals carries a fine tomentum, but the margins are not particularly distinctive.

As the first petal opens, it is from small to average in size, of medium length and ovoid. The color on the outside of the petal is near Dark Red, 5R3/7. The inner surface is more vibrant than a color near Dark Reddish Orange, 7.5R4/11.

The bud opens up well, and is not retarded or prevented from opening by cold, hot, wet, or dry weather.

BLOOM

The size of the bloom when fully open is average, being from 6 to 8 centimeters in diameter. The petalage is double, with from 35 to 45 petals, plus 3 to 8 petaloids arranged regularly. The petals are cupped and full at first, becoming open to high centered.

The petals remain at first tightly cupped, with tips reflexed slightly outward. Later, at maturity, the petals become more loosely cupped, with tips reflexed slightly outward and margins undulated.

The petals are relatively thick and moderately leathery, with inside slightly velvety and outside slightly shiny to satiny. The outside and intermediate petals are broadly obovate, with undulated margins. Inside petals are obovate to irregular, and slightly undulated. The colors may be modified by being blotched, shaded and/or washed with other colors.

The paragraphs immediately following describe color values observed in a flower newly opened in the month of November. The plant had been grown outdoors, in Ontario, Calif.

The outside surface of the outside petal has a color between Strong Red, 2.5R5/12, and Strong Red, 5R4/12, only more vibrant. The outside surface of the intermediate petal and of the inner petal are of the same coloration.

The inside surface of the outside petal has a color near Strong Reddish Orange, 7.5R5/13, only more vibrant. The same coloration applies to the inside surface of the intermediate petals and of the inside surface of the inner petals.

The color values observed in a bloom which had been open for three days, outdoors, in the month of November, were the same as those of the newly opened bloom. The plant had been grown outdoors, in Ontario, Calif.

The general color effect of both the newly opened flower and the flower which had been three days open was a color near Strong Reddish Orange, 7.5R5/13, but much more vibrant. The petals drop off cleanly, except for petaloids. There is no noticeable degree of fading before the petals fall, and they are not particularly affected by cold, hot, wet or dry weather.

The flower on the bush in the garden persists for more than five days in the month of November, in the locality named. Cut roses grown outdoors and kept at living-room temperature will last from four to six days in the month of November.

REPRODUCTIVE ORGANS

The stamens are average in number and arranged regularly about the pistils.

The filaments are medium length, most of them with anthers.

The anthers are from small to medium size, all opening approximately at once. The color of the margins is near Vivid Yellow, 2.5Y8/12, as the buds open.

There is a moderate amount of pollen, which is near Vivid Yellow, 2.5Y8/12, in color.

The pistils are approximately 75 in number, this being average.

The styles are moderately even, average length to long, average in caliper and somewhat bunched.

The stigma is near Pale Orange Yellow, 7.5YR9/4, in color.

Usually the ovaries are enclosed in the calyx.

The hips are from short to average in length and globular in form. The color of the mature hip is between Strong Reddish Orange, 10R5/11, and Dark Reddish Orange, 10R4/9. They are smooth with thick, fleshy walls.

The sepals fall soon.

The new variety produces from few to an average number of seeds, from 6 to 12, which are small in size.

FOLIAGE

The compound leaves usually comprise three to seven leaflets. They are of medium size, moderately heavy to somewhat leathery and glossy. The leaflets are ovate in shape with apex acute, base obtuse and margin irregularly serrate.

The mature foliage displays upon its upper surface a coloration which is between Moderate Olive Green, 5GY4/3, and Grayish Olive Green, 5GY3/2. The under surface is between Moderate Yellow Green, 2.5GY5/5, and Moderate Olive Green, 2.5GY4/3, highly overlaid with light gray.

The young foliage on its upper surface has a ground color near Moderate Yellow Green, 5GY5/6, but is heavily overlaid with a color near Dark Red, 2.5R3/7. The under surface has a ground color between Strong Yellow Green, 5GY7/10, and Strong Yellow Green, 5GY6/8, but is also highly overlaid, except along the midribs, with a color near Dark Red, 2.5R3/7.

The rachis is average in size. The upper side is grooved, with many tiny stipitate glands on the edges, while the underside is generally smooth, except for a few sparse prickles.

The stipules are finely serrated along their lateral margins, are medium to long in length and medium in breadth, with medium-length points turning out at an angle of usually less than 45°.

The plant is resistant to mildew, when compared with other varieties now in commerce grown under comparable conditions in the locality named.

GROWTH

The plant is low, bushy, and much branched. Its growth is from free to vigorous. The canes are medium in caliper.

The main stems are near Moderate Olive Green, 2.5GY4/3, in color. They carry several sharply pointed large prickles, which are medium to long in length, almost straight to hooked slightly downward, with medium-length, moderately broad bases. There are few small prickles, and the coloration of both large and small prickles is Moderate Brown, 7.5YR4/5, aging to gray. There are no hairs.

The branches are near Moderate Yellow Green, 2.5GY5/5, in color. They carry several sharply pointed large prickles, of short to medium length, which are hooked slightly downward and have short to medium-length, moderately broad bases. These large prickles, as well as the few small prickles, are near Strong Yellowish Brown, 10YR5/6, in color. There are no hairs.

New shoots are near Strong Yellow Green, 5GY6/8, in color. They carry several sharply pointed large prickles, which are medium-length to long, hooked slightly downward, with medium-length, moderately broad bases. There are few small prickles, and both large and small prickles are the same coloration as the new shoots, slightly overlaid with a color near Moderate Red, 2.5R4/10.

I claim:

1. The new and distinct variety of Floribunda bush rose plant substantially as herein illustrated and described, which is characterized most especially in its high resistance to mildew and in that the rich orange scarlet color of its blooms persists substantially without change from the opening of the bud until the petals fall, said blooms being double, with from about 35 to about 45 petals and from six to eight petaloids.

* * * * *

UNITED STATES PATENT AND TRADEMARK OFFICE

CERTIFICATE OF CORRECTION

PATENT NO. : PP-4297

DATED : September 5, 1978

INVENTOR(S) : Samuel McGredy, IV

It is certified that error appears in the above-identified patent and that said Letters Patent are hereby corrected as shown below:

In the heading, above column 1:

"EXEMPLARY CLAIM" should read --Abstract

Signed and Sealed this

*Fifteenth* Day of *May 1979*

[SEAL]

*Attest:*

RUTH C. MASON
*Attesting Officer*

DONALD W. BANNER
*Commissioner of Patents and Trademarks*